United States Patent
Mouri et al.

(10) Patent No.: US 9,303,062 B2
(45) Date of Patent: Apr. 5, 2016

(54) SOLID OXIDIZED GLUTATHIONE SALT AND METHOD FOR PRODUCING SAME

(75) Inventors: Taku Mouri, Takasago (JP); Naoaki Taoka, Takasago (JP); Tadashi Moroshima, Takasago (JP); Koichi Kinoshita, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 14/129,474

(22) PCT Filed: Jun. 28, 2012

(86) PCT No.: PCT/JP2012/066510
§ 371 (c)(1),
(2), (4) Date: Feb. 10, 2014

(87) PCT Pub. No.: WO2013/002317
PCT Pub. Date: Jan. 3, 2013

(65) Prior Publication Data
US 2014/0194371 A1 Jul. 10, 2014

(30) Foreign Application Priority Data

Jun. 30, 2011 (JP) ................................. 2011-146574

(51) Int. Cl.

| A61K 38/05 | (2006.01) |
|---|---|
| C07K 7/02 | (2006.01) |
| A23L 1/305 | (2006.01) |
| C07K 5/02 | (2006.01) |
| A61K 8/64 | (2006.01) |
| A61Q 19/00 | (2006.01) |
| C05F 11/00 | (2006.01) |
| A23L 2/52 | (2006.01) |
| A61K 38/00 | (2006.01) |

(52) U.S. Cl.
CPC . *C07K 7/02* (2013.01); *A23L 1/305* (2013.01); *A23L 2/52* (2013.01); *A61K 8/64* (2013.01); *A61Q 19/00* (2013.01); *C05F 11/00* (2013.01); *C07K 5/0215* (2013.01); *A61K 38/00* (2013.01); *Y02E 50/343* (2013.01); *Y02W 30/47* (2015.05)

(58) Field of Classification Search
CPC ......... B43L 11/055; A23L 1/305; A23L 2/52; A61K 38/00; A61K 8/64; A61Q 19/00; C05F 11/00; C07K 5/0215; C07K 7/02
See application file for complete search history.

(56) References Cited

U.S. PATENT DOCUMENTS

| 3,482,025 | A | * | 12/1969 | Kawashima et al. .......... 514/419 |
|---|---|---|---|---|
| 6,165,979 | A | * | 12/2000 | Kozhemyakin et al. ....... 514/1.4 |
| 6,251,857 | B1 | | 6/2001 | Kozhemyakin et al. |
| 6,312,734 | B1 | | 11/2001 | Kozhemyakin et al. |
| 7,094,870 | B2 | | 8/2006 | Shimose et al. |
| 7,169,412 | B2 | | 1/2007 | Kozhemyakin et al. |
| 7,371,411 | B2 | | 5/2008 | Kozhemyakin et al. |
| 2002/0016288 | A1 | | 2/2002 | Kozhemyakin et al. |
| 2003/0077334 | A1 | | 4/2003 | Kozhemyakin et al. |
| 2004/0250751 | A1 | | 12/2004 | Shimose et al. |
| 2005/0054580 | A1 | | 3/2005 | Kozhemyakin et al. |
| 2007/0123450 | A1 | | 5/2007 | Kozhemyakin et al. |
| 2007/0142267 | A1 | | 6/2007 | Kozhemyakin et al. |
| 2008/0220093 | A1 | | 9/2008 | Kozhemyakin et al. |

FOREIGN PATENT DOCUMENTS

| CN | 1498111 A | 5/2004 |
|---|---|---|
| JP | 41 14997 | 8/1941 |
| JP | 42 001393 | 1/1967 |
| JP | 05 146279 | 6/1993 |
| JP | 07 177896 | 7/1995 |
| JP | 2002 538079 | 11/2002 |
| WO | 03 035674 | 5/2003 |

OTHER PUBLICATIONS

Sigma "L-Glutathione oxidized disodium salt" date Sep. 2002, accessed online https://www.sigmaaldrich.com/content/dam/sigma-aldrich/docs/Sigma/Product_Information_Sheet/2/g6654pis.pdf on Dec. 20, 2014, 1 page.*
Sugimura, Y., et al. "Effect of orally Administered Reduced- and Oxidized-Glutathione against Acetaminophen-Induced Liver Injury in Rats", J Nutr Sci Vitaminol, vol. 44, pp. 613-624, (1998).
Jelsch, C., et al., "The oxidized form of glutathione", ACTA Crystallographica Section C, vol. C55, No. 9, pp. 1538-1540 (1999).
International Search Report Issued Sep. 4, 2012 in PCT/JP12/066510 Filed Jun. 28, 2012.
The Extended European Search Report issued Jan. 8, 2015, in Application No. / Patent No. 12803619.1-1453 / 2727932.

* cited by examiner

*Primary Examiner* — Marcela M Cordero Garcia
(74) *Attorney, Agent, or Firm* — Oblon, McClelland, Maier & Neustadt, L.L.P.

(57) ABSTRACT

A solid oxidized glutathione salt is produced by heating an oxidized glutathione at 30° C. or higher while the oxidized glutathione is brought into contact with an aqueous medium in the presence of a substance for providing a cation, to produce the salt of the oxidized glutathione and the cation as a solid, wherein the aqueous medium is composed of water and/or a water-soluble medium, and the cation is at least one selected from an ammonium cation, a calcium cation and a magnesium cation.

20 Claims, No Drawings

SOLID OXIDIZED GLUTATHIONE SALT AND METHOD FOR PRODUCING SAME

TECHNICAL FIELD

The present invention relates to a technology of improving the handling property of oxidized glutathione. Oxidized glutathione is useful as a health food product, a pharmaceutical product, a cosmetic product, a fertilizer product and the like or an intermediate for producing the products.

BACKGROUND ART

Oxidized glutathione (GSSG) is useful in fields of health foods, pharmaceuticals, cosmetics, fertilizers and the like as well as reduced glutathione (GSH). For example, it is known that oxidized glutathione has detoxication or the like (Non-patent Document 1 and others).

Oxidized glutathione (GSSG) has a molecular structure obtained by oxidizing two molecules of reduced glutathione (GSH) to form a disulfide bond, and reduced glutathione is a tripeptide composed of glutamic acid, cystein and glycine, that is, "L-γ-glutamyl-L-cysteinyl-glycine".

As a method for producing oxidized glutathione, for example, there is known a method for producing oxidized glutathione in the form of an aqueous solution by first preparing an aqueous solution or yeast extract containing reduced glutathione with a fermentation method, and oxidizing the aqueous solution or yeast extract (Patent Document 1, Patent Document 2 and others). The oxidized glutathione obtained in the above-mentioned manner is powdered as an oxidized glutathione-containing yeast extract powder by, for example, adding an excipient or the like to the aqueous solution, followed by freeze-drying or spray-drying. However, depending on the uses thereof, it may not be allowed to use an excipient and use of an excipient may be limited in some cases.

Conventionally, as the oxidized glutathione which is obtained in the form of a solid without using an excipient, for example, a powder of oxidized glutathione anhydride is known. Such a powder is obtained by separating and purifying oxidized glutathione from the above-described aqueous solution of oxidized glutathione, followed by freeze-drying, spray-drying or the like. In addition, three forms of oxidized glutathione are known, that is, oxidized glutathione hydrate and oxidized glutathione salt in addition to the anhydrate. However, the forms of oxidized glutathione have various problems in terms of industrial uses.

For example, oxidized glutathione anhydride has a problem of having extremely high hygroscopicity and deliquescency. In order to avoid moisture absorption and deliquescence, for example, the anhydride is required to be cooled or frozen, or alternatively kept in a specially wrapped state for preventing moisture absorption at the time of preservation, transportation, distribution and the like. In any cases, the anhydride is unsuitable for large supply in an industrial level. In addition, the anhydride is highly water-soluble so that the anhydride is used for an aqueous solution product such as a medical agent for injection, but is easy to be converted into hydrate in water. The hydrate has low solubility in water, and there is a risk that the crystal thereof is precipitated in the aqueous solution product.

As oxidized glutathione hydrate, a crystal of oxidized glutathione octahydrate (Non-patent Document 2) and a crystal of oxidized glutathione monohydrate (Patent Document 3) are known. A crystal of oxidized glutathione octahydrate easily releases crystal water and is difficult to keep the water amount in the crystal at a constant level and thus inferior in stability. Also, the octahydrate is insufficient in reproduction and unsuitable for large-scale synthesis or industrialization. A crystal of oxidized glutathione monohydrate is low deliquescent; on the other hand, the monohydrate is difficult to be handled in the form of an aqueous solution owing to low solubility in water, and thus it is impossible to produce an aqueous solution product of the monohydrate with a high concentration. In addition, when oxidized glutathione is produced, a base is generally used and it is necessary to remove the base in order to precipitate the monohydrate. Therefore, it is required to use, for example, an ion exchange resin or a chelating resin. However, in the case of the treatment with such resins, environmental burdens, such that a large quantity of a waste solution is generated and the treatment therefor is required, are increased, and there is a problem in terms of the cost.

As an oxidized glutathione salt, salts of a metal and an amino acid are known. As a metal salt of oxidized glutathione, an oxidized glutathione disodium salt is commercially available and additionally an alkali metal salt such as a dilithium salt of oxidized glutathione (Patent Document 4) is known. In addition, an amino acid salt such as a monoornithine salt of oxidized glutathione (Patent Document 5) and a monolysine salt of oxidized glutathione (Patent Document 6) are so far reported. However, there are few examples of being isolated. An alkali metal salt of oxidized glutathione such as a disodium salt of oxidized glutathione and a dilithium salt of oxidized glutathione is difficult to be made available in the form of a solid in the first place. In addition, such an alkali metal salt has extremely high deliquescency and is unsuitable for industrial use similarly to oxidized glutathione anhydride. Further, with respect to an amino acid salt such as a monoornithine salt of oxidized glutathione and a monolysine salt of oxidized glutathione, for example, there is a problem that the amino acid salt has the same functional group as that of oxidized glutathione, and therefore the amino acid causes a competitive reaction to inhibit the aimed reaction when the salt is subjected to the reaction. In addition, there is another problem that an amino acid is physiologically active substance, and therefore addition of the salt to a final product is often limited.

PRIOR ART

Patent Document

Patent Document 1: JP H5-146279 A
Patent Document 2: JP H7-177896 A
Patent Document 3: WO 2003/035674
Patent Document 4: JP 2002-538079 T
Patent Document 5: JP S42-1393 B
Patent Document 6: JP S41-14997 B

Non-Patent Document

Non-patent Document 1: Yoichiro Sugimura et al., "Effect of Orally Administered Reduced- and Oxidized-Glutathione against Acetaminophen-Induced Liver Injury in Rats", J. Nutr. Sci. Vitaminol., vol. 44, pp. 613-624 (1998)

Non-patent Document 2: Christian Jelsch et al., "The oxydized form of glutathione", Acta Cryst., vol. C55, No. 9, pp. 1538-1540 (1999)

DISCLOSURE OF THE INVENTION

Problems to be Solved by the Invention

The present invention was completed in view of the above-described circumstances, and the objective of the present invention is to provide a solid oxidized glutathione which is low in deliquescency and is easily handled, and at the same time, is highly water-soluble and scarcely limited in uses.

More specifically, conventional oxidized glutathione in the form of a solid has problems such as high deliquescency and low water solubility as described above. In addition, examples of oxidized glutathione obtained by solidification together with an excipient and solidification in the form of amino acid salt are known; however, the uses thereof may be limited in some cases. Therefore, it can be thought to obtain a solid with low deliquescency and high water solubility from an inorganic salt of oxidized glutathione, which is less limited in the use thereof; however, it is not easy to isolate an inorganic salt of oxidized glutathione in the form of a solid. For example, it is described in Patent Document 4 that an oxidized glutathione diammonium salt is formed in the middle of the process for producing an oxidized glutathione dilithium salt from reduced glutathione; however, the ammonium salt is not isolated in the form of a solid. In Patent Document 4, oxidized glutathione anhydride in the form of a solid is obtained by adjusting the pH of an aqueous solution of the ammonium salt to be 5 and freeze-drying the solution. However, an oxidized glutathione ammonium salt is not isolated, though it is assumed that oxidized glutathione and ammonia continuously form a salt even in the stage where the pH of the aqueous solution of the ammonium salt is adjusted to be 5 since isoelectric point of oxidized glutathione is around pH 2.8. Furthermore, from the result of the experiment by the inventors of the present invention, it was clarified that an oxidized glutathione diammonium salt can not be obtained in the form of a solid by a conventionally known method. In detail, the inventors tried to obtain the solid by adding 2 molar of ammonia to 1 molar of oxidized glutathione to obtain an aqueous solution of which pH was 5, and freeze-drying the solution; however, the freeze-dried product became oily when being heated back to room temperature. Under such circumstances, it has been desired to obtain an oxidized glutathione salt that has low deliquescency and high water solubility, which have not been achieved so far, and that is easy to be produced and distributed in a commercial scale.

Means for Solving the Problems

The inventors of the present invention intensively studied for solving the above problem. As a result, the present inventors completed the present invention by finding that only an ammonium cation, a calcium cation and a magnesium cation can form a solid salt with oxidized glutathione by the production method in the specific heating condition, and any of the thus obtained solid oxidized glutathione salt has low deliquescency and high water solubility.

The solid oxidized glutathione salt of the present invention can be produced by a method comprising the step of heating an oxidized glutathione at 30° C. or higher while the oxidized glutathione is brought into contact with an aqueous medium in the presence of a substance for providing a cation, to produce the salt of the oxidized glutathione and the cation as a solid, wherein the aqueous medium is composed of water and/or a water-soluble medium, and the cation is at least one selected from an ammonium cation, a calcium cation and a magnesium cation. For example, the time for heating at a temperature of 30° C. or higher is 0.25 hours or longer. As the water-soluble medium, an alcohol medium such as methanol, ethanol, propanol and butanol, a ketone medium such as acetone and methyl ethyl ketone, and the like are preferred.

The solid oxidized glutathione salt of the present invention is characterized in comprising oxidized glutathione and at least one cation selected from an ammonium cation, a calcium cation and a magnesium cation, wherein the solid oxidized glutathione salt is in a solid state at room temperature. The solid oxidized glutathione salt is kept in a solid state after mechanical impact is given, and does not deliquesce when the solid oxidized glutathione salt is kept in a condition of temperature of 25° C., ordinary pressure and relative humidity of 75% RH for 2 hours or longer. The examples of the solid oxidized glutathione salt include a monoammonium salt of oxidized glutathione, a hemicalcium salt or a monocalcium salt of oxidized glutathione, and a hemimagnesium salt or a monomagnesium salt of oxidized glutathione.

In the range of the present invention, a powder formulation comprising the above-described solid oxidized glutathione salt, wherein a content of oxidized glutathione in the form of solid is 0.01 mass % or more, and a liquid formulation wherein the above-described solid oxidized glutathione salt is dissolved or dispersed in water or an organic medium containing water are included. The organic medium is exemplified by an alcohol medium, a ketone medium, an aldehyde medium, an ester medium, a hydrocarbon medium, a sulfoxide medium, an ether medium and the like.

Effect of the Invention

According to the present invention, a solid oxidized glutathione salt can be obtained easily by using the specific cation and treating oxidized glutathione with the production method in the specific heating condition.

In addition, according to the present invention, the solid oxidized glutathione can be provided which is low in deliquescency and is easily handled, and at the same time, is highly water-soluble and scarcely limited in uses, since the oxidized glutathione salt is formed with the specific cation.

MODE FOR CARRYING OUT THE INVENTION

The objective of the present invention is to precipitate a salt of oxidized glutathione in the form of a solid from a solution containing oxidized glutathione.

Oxidized glutathione which is usable as a raw material is not particularly limited, and for example, commercially available oxidized glutathione may be used, oxidized glutathione which is obtained by oxidizing reduced glutathione obtained with a conventional method such as a fermentation method may be used, and oxidized glutathiones except for the oxidized glutathiones described above may be used.

The above-described oxidation reaction proceeds by an oxidizing agent in an appropriate solvent such as water. Such an oxidizing agent is exemplified by a weak oxidizing agent such as oxygen; and a strong oxidizing agent such as hydrogen peroxide, iodine and potassium ferrocyanide. As other oxidizing agent, a gaseous substance such as a nitrogen oxide substance and a sulfoxide substance may be used. In the oxidation reaction, an oxidation catalyst such as copper sulfate, iron sulfate and iron (III) chloride may be used, if necessary. It is recommended to adjust the pH of the reaction mixture in the oxidation reaction, and for example, the pH is desirably adjusted to not less than 5 and not more than 12, preferably not less than 6 and not more than 10, and more preferably not less than 7 and not more than 9. By adjusting the pH within the above-described range, reduced glutathione and oxidized glutathione can be stabilized and the reaction speed can be increased.

Oxidized glutathione may be isolated from the oxidized glutathione solution obtained in the above-described oxidation reaction and may be further purified if necessary. Then, the isolated product or purified product may be used as the above-described oxidized glutathione raw material. Alternatively, the oxidized glutathione solution may be directly used as the oxidized glutathione raw material without carrying out post-treatment such as isolation or purification. In such an isolation procedure, for example, concentration, dilution, filtration and the like of the solution are carried out.

In the present invention, the inventors intensively studied for accomplishing the above-described objective and could achieve the above-described objective by founding that when oxidized glutathione is heated to temperature of 30° C. or higher with bringing the oxidized glutathione into contact with an aqueous medium in the presence of a substance which can provide at least one kind of cation selected from an ammonium cation, a calcium cation and a magnesium cation, the salt thereof can be produced in the form of a solid. For example, if a sodium cation or a lithium cation is used as the cation, no salt is produced in the form of a solid even if oxidized glutathione is heated to a temperature of 30° C. or higher. In addition, no salt is produced in the form of a solid also when oxidized glutathione is not heated to a temperature of 30° C. or higher. It was found that an inorganic salt of oxidized glutathione is produced in the form of a solid by combining the specified cation and the specified treatment condition.

The examples of the above-described substance for providing the above-described cation include a base which is exemplified by an ionic ammonium-containing compound, such as ammonia such as ammonium hydroxide, an ammonium halide such as ammonium chloride and ammonium bromide, an ammonium carbonate such as ammonium carbonate and ammonium hydrogencarbonate, ammonium phosphate, ammonium sulfate and ammonium acetate; an ionic calcium-containing compound, such as calcium hydroxide, a calcium halide such as calcium chloride, a calcium carbonate such as calcium carbonate and calcium hydrogencarbonate; an ionic magnesium-containing compound, such as magnesium hydroxide, a magnesium halide such as magnesium chloride, a magnesium carbonate such as magnesium carbonate and magnesium hydrogencarbonate, magnesium sulfate. A preferred base is a base of which component other than ammonia, calcium and magnesium can become gas or water, such as ammonia, ammonium hydroxide, an ammonium carbonate salt, calcium hydroxide, a calcium carbonate salt, magnesium hydroxide and a magnesium carbonate salt; and a particularly preferred base is a hydroxide substance such as ammonium hydroxide, i.e. ammonia water, calcium hydroxide and magnesium hydroxide. The cation-producing substance, particularly a base, may be used alone or in a proper combination.

By forming a salt of a cation other than the above-described ammonium, calcium and magnesium with oxidized glutathione, and exchanging the cation species, an ammonium salt, a calcium salt or a magnesium salt may be formed. For the exchange of the cation species, a means is not particularly limited, and for example, a solubility difference and an equilibrium relation may be utilized.

The amount of the cation-producing substance to be used can be set properly depending on the amount of the cation which is contained in the solid oxidized glutathione salt to be produced, and generally, the mole ratio between the used cation and the used oxidized glutathione is the same as that in the solid. Therefore, the amount, i.e. mole ratio, of the cation to be used relative to the oxidized glutathione is often set in the range which is the same as that in the solid as described below.

The above-described aqueous medium includes water and/or a water-soluble medium, particularly a water-soluble organic medium. Such a water-soluble organic medium is exemplified by an alcohol medium such as methanol, ethanol, propanol, butanol and ethylene glycol; a ketone medium such as acetone and methyl ethyl ketone; an ether medium such as tetrahydrofuran and dioxane; an ester medium; a nitrile medium such as acetonitrile; an amide medium such as N,N-dimethylformamide and acetamide; and an alcohol medium and a ketone medium are preferred. The water-soluble organic medium may have a carbon number of, for example, 5 or less, preferably 3 or less, and more preferably 1. In consideration of utilization in the fields of foods and the like, the aqueous medium is preferably water, acetone, ethanol or the like, particularly water or ethanol, and in the use other than foods, for example, fertilizers, methanol may be selected as a preferred aqueous medium in addition to the above media. The water-soluble organic medium may be, for example, a medium which can be mixed at a ratio of 100 parts by mass or more based on 100 parts by mass of water at a temperature of 25° C., or a medium which can be mixed with water at any ratio.

The above-described aqueous medium may be used alone or in a proper combination of two or more thereof, and it is recommended that the aqueous medium may be used in combination of water and a water-soluble medium. In such a case, water functions as a good solvent for oxidized glutathione and the water-soluble medium functions as a poor solvent. The ratio of the water-soluble medium based on 10 parts by volume of water is, for example, not less than about 1 and not more than about 1000 parts by volume, preferably not less than about 5 and not more than about 500 parts by volume, more preferably not less than about 10 and not more than about 100 parts by volume, and particularly preferably not less than about 12 and not more than about 50 parts by volume.

The mass ratio, such as a concentration, of oxidized glutathione relative to the total mass of the aqueous medium and the oxidized glutathione is not particularly limited, and for example, the production is preferably carried out in a range of 0.1 mass % or higher and 60 mass % or less. In terms of the viewpoints of productivity and operability, the lower limit thereof is preferably 1 mass % or higher, more preferably 5 mass % or higher, and particularly preferably 8 mass % or higher form the viewpoint of production efficiency. In addition, in consideration of the viscosity or the like of the solution, the upper limit thereof is preferably 40 mass % or less, and more preferably 30 mass % or less.

In the present invention, if necessary, a solvent other than the above-described aqueous media may be used in combination with the aqueous media to an extent that no adverse effect is caused on the solidification of the oxidized glutathione salt.

In addition, in the present invention, an acid may be used if necessary. For example, when an amount of the cation-producing substance is used excessively relative to oxidized glutathione, the unnecessary cation-producing substance may be neutralized with an acid thereafter. A usable acid is not particularly limited, and a mineral acid such as hydrochloric acid and sulfuric acid is preferred in consideration of cost and removal easiness.

A proper value of the pH of the aqueous medium at the time of producing oxidized glutathione in the form of a solid is changed depending on the temperature, the presence or absence of the water-soluble medium and the amount thereof, and therefore the proper value is difficult to be determined in general. However, the lower limit of the pH is desirably, for example, 2.8 or higher, preferably 3.0 or higher, more preferably 3.2 or higher, and the upper limit of the pH is desirably, for example, 7.0 or lower, preferably 6.0 or lower, more preferably 5.5 or lower.

The heating temperature is not particularly limited as long as the temperature is 30° C. or higher, and is preferably 33° C. or higher, more preferably 35° C. or higher, and particularly preferably 40° C. or higher. If the heating temperature is lower than 30° C., it is impossible to obtain the target salt of oxidized glutathione as a solid such that the salt is not solidified and remains in an oily state even if time passes. In addition, in consideration of the workability in industrial scale in which the amount of the aqueous medium to be used is, for example, 10 kg or more, preferably 100 kg or more, further preferably 500 kg or more, and 30 ton or less, preferably about 10 ton or less, the heating temperature is more preferably higher than 45° C. and particularly preferably 48° C. or higher. Even if the heating temperature is 30° C. or higher, depending on other conditions, a mixture of the solidified product and the oily product may be precipitated in an emulsified state and it may result in difficulty of stirring in the case of production in industrial scale in some cases. However, the precipitation ratio of the solid can be increased and the emulsified state can be prevented by setting the heating temperature to 45° C. or higher. The upper limit of the heating temperature is not particularly limited, but the upper limit is preferably the boiling point or lower of the aqueous medium in terms of safety since high pressure is not needed. In addition, as the heating temperature is higher, precipitation of a prescribed amount of the oxidized glutathione salt tends to take longer time. From such a viewpoint, the heating temperature is, for example, 80° C. or lower, preferably 70° C. or lower, and particularly preferably 60° C. or lower. In particular, from the viewpoint of both precipitation speed and the property of the oxidized glutathione salt to be obtained in industrial scale production, the heating temperature is particularly preferably in a range of not less than 53° C. and not more than 60° C.

In addition, the heating treatment is generally carried out under normal pressure, but may be carried out under increased pressure condition or reduced pressure condition.

The heating time may be set properly in a range necessary for the solidification of the oxidized glutathione salt, and the proper time is changed depending on the heating temperature and is thus generally difficult to be determined. However, the lower limit thereof is, for example, 0.25 hours or longer, preferably 0.5 hours or longer, and more preferably 1 hour or longer. When the heating temperature is especially high, for example, when the temperature is 45° C. or higher, or in a case of industrial scale production, the heating time may be preferably 2 hours or longer, and further preferably 3 hours or longer in some cases. The upper limit thereof is, for example, 48 hours or shorter, preferably 24 hours or shorter, and more preferably 10 hours or shorter. It is more preferred to keep the mixture at 30° C. or higher for the above-exemplified duration from start of the solidification of the oxidized glutathione salt.

During the heating treatment, it is desirable to bring oxidized glutathione and the aqueous medium into contact with each other in a stirring condition, and the stirring intensity is not particularly limited. As a agitation power, the lower limit thereof is generally 0.001 kW/m$^3$ or higher, preferably 0.03 kW/m$^3$ or higher, more preferably 0.2 kW/m$^3$ or higher, and the upper limit thereof is 5 kW/m$^3$ or lower, preferably 2 kW/m$^3$ or lower, and more preferably 1 kW/m$^3$ or lower.

In the present invention, it is sufficient that oxidized glutathione is heated to a temperature of 30° C. or higher in the presence of a prescribed cation-producing substance while being brought into contact with the aqueous medium, and the process for allowing the condition to be realized is not particularly limited. For example, the mixing procedure of the cation-producing substance, the oxidized glutathione and the aqueous medium is not particularly limited, and the components may be mixed in arbitrary procedure. Even in the case where the aqueous medium is composed of two or more media, the mixing procedure and timing is set properly.

In a preferable operational procedure,
first mixing: the prescribed cation-producing substance and oxidized glutathione are mixed with water, preferably oxidized glutathione and the cation-producing substance are dissolved in water; and then,
second mixing: the obtained first mixed liquid is further mixed with a water-soluble medium which is a poor solvent, if necessary.

In the first mixing, it is desirable that either one of the cation-producing substance and oxidized glutathione, preferably both, is previously dissolved in water to obtain a solution, followed by mixing. In the second mixing, a water-soluble medium may be added to the first mixed solution, or the first mixed solution may be added to a water-soluble medium, or the first mixed solution and a water-soluble medium may be added at the same time to another container.

In the above-described preferred operation procedure, the timing of heating to a temperature of 30° C. or higher may be set properly, and the timing may be any one of before the first mixing, during the first mixing, after the first mixing and before the second mixing, during the second mixing, and after the second mixing. It is most preferred that the temperature is raised to 30° C. or higher at the latest before start of the second mixing, and thereafter the heating temperature is kept.

The process for the solidification of the oxidized glutathione salt after the temperature is raised to 30° C. or higher is not also particularly limited, and various processes may be performed. For example,
an example 1: the solid oxidized glutathione salt can be precipitated from a solution containing oxidized glutathione;
an example 2: oxidized glutathione can be separated as an oily product (oil out) or a gel-like product from a solution or slurry containing oxidized glutathione, and thereafter the oily product or the gel-like product can be solidified; and
an example 3: the oxidized glutathione salt can be solidified while the solvent is removed from a solution or a slurry containing oxidized glutathione.

In the case of the example 1: solid precipitation, specifically, oxidized glutathione can be precipitated in the form of a solid from the second mixed solution in which oxidized glutathione is dissolved. For example, in the case of the above-described most preferred heating timing, i.e. when heating is started before the second mixing, in general, the oxidized glutathione salt is precipitated as a solid. In addition, even in the case of heating to a temperature of 30° C. or higher after start of the second mixing, the oxidized glutathione salt may be precipitated as a solid unless start of the heating is too late. Further, depending on the heating temperature or the mixing speed of the second mixing, the oxidized glutathione salt starts to precipitate as a solid during the second mixing, and the mixing may be carried out while producing a slurry in some cases.

In the case of the example 1: solid precipitation, if necessary, a seed crystal may be added to promote the solidification of the oxidized glutathione salt.

As the example 2: solidification of oily product or gel-like product, the above-described case in which heating to a temperature of 30° C. or higher after start of the second mixing is specifically exemplified. As the start of the heating is delayed, an oily product (oil out) or a gel-like product easily tends to be produced. Even in such a case, if heating to a temperature of 30° C. or higher is continued, the oily product or the gel-like product is solidified. From an industrial viewpoint, when the oily product is subjected to heating treatment, it is necessary to pay attention to occurrence of an undesirable incident such as inclusion of a solvent or lumps formation.

In the example 1: solid precipitation and the example 2: solidification of oily product and gel-like product, the solid oxidized glutathione salt may be separated from the aqueous medium by common solid-liquid separation operation such as filtration under increased pressure, centrifugal separation, centrifugal precipitation and decantation. The separated solid oxidized glutathione salt may be subjected to common drying operation such as vacuum drying and ventilation drying, if necessary. In addition, the solid oxidized glutathione salt is dissolved again in the aqueous medium and re-solidified, such as re-crystallized and re-coagulated, again under the same heating treatment conditions as the above to purify the oxidized glutathione salt.

As the example 3: solvent removal and solidification, a method of utilizing spray drying can be exemplified. Specifically, the solid oxidized glutathione salt can be also obtained by spraying the first mixed solution or the second mixed solution into a high temperature gas and removing the solvent while the mixed solution is heated to a temperature of 30° C. or higher.

The above process may be optimized properly depending on the kind of the cation-producing substance. For example, when an oxidized glutathione ammonium salt is solidified by using an ionic ammonium-containing compound, it is most preferred to add a water-soluble medium as a poor solvent while an aqueous solution containing an ammonium salt of oxidized glutathione is heated to a temperature of 30° C. or higher. The duration time of adding the water-soluble medium is not particularly limited, and for example, the duration time is generally 5 minutes or longer, preferably 10 minutes or longer, and in consideration of productivity, the duration time is 30 hours or shorter, preferably 20 hours or shorter, and particularly preferably 10 hours or shorter. On the other hand, when a calcium salt or a magnesium salt of oxidized glutathione is solidified by using an ionic calcium-containing compound or an ionic magnesium-containing compound, from the viewpoint of easiness for solidification, it is more preferred to add a solution, particularly an aqueous solution, in which oxidized glutathione and the cation-producing substance, i.e. an ionic calcium-containing compound and/or an ionic magnesium-containing compound, are dissolved into the water-soluble medium as a poor solvent than addition in the reverse direction, but the addition direction can be selected depending on the necessity.

According to the above-described method, the oxidized glutathione salt can be obtained in the form of a solid. The yield amount as a solid is, for example, 80 mass % or higher, preferably 90 mass % or higher, and more preferably 95 mass % or higher, based on the used amount of oxidized glutathione.

The oxidized glutathione salt obtained as described above is composed of oxidized glutathione and at least one kind cation selected from an ammonium cation, a calcium cation and a magnesium cation, and can keep the solid state thereof at room temperature, e.g. 25° C. The amount ratio of the cation and oxidized glutathione may be set properly depending on the valence number of the cation. When the mole amount of the cation is defined as $C_1$, the valence number of the cation is defined as $n_1$, and the mole amount of glutathione is defined as G, the ratio of $n_1 \times C_1$ to G (former/latter) is, for example, not less than about 0.5 and not more than about 4, preferably not less than about 0.7 and not more than about 3, and more preferably not less than about 1 and not more than about 2. When a plurality of different cations exist, it is recommended that the ratio of the sum of the products ($n_1 \times C_1 + n_2 \times C_2 + n_3 \times C_{3+} \ldots$) of the mole amounts of respective cations ($C_1, C_2, C_3, \ldots$) and the valence number of respective cations ($n_1, n_2, n_3 \ldots$) relative to the mole amount G of glutathione (former/latter) is within the above-mentioned range.

In the case of an ammonium salt of oxidized glutathione, the mole ratio of ammonia relative to oxidized glutathione (former/latter) is preferably not less than 1 and not more than 4, more preferably not less than 1 and not more than 3, furthermore preferably not less than 1 and not more than 2, and particularly preferably 1. In the case of a calcium salt or a magnesium salt of oxidized glutathione, the mole ratio of either calcium or magnesium relative to oxidized glutathione (former/latter) is preferably not less than 0.5 and not more than 2, more preferably not less than 0.5 and not more than 1.5, furthermore preferably not less than 0.5 and not more than 1, and particularly preferably 0.5 or 1.

The solid oxidized glutathione salt obtained as described above has low deliquescency and high water solubility. The deliquescency of the solid oxidized glutathione can be evaluated by allowing a powder of the salt to stand in an environment at a temperature of 25° C., normal pressure, e.g. 1 atmospheric pressure, and a relative humidity of 75% RH, and observing whether deliquescence starts or not with naked eyes. The oxidized glutathione of the present invention does not start to deliquesce, even if being allowed to stand in the above-described conditions, for example, for 2 hours, preferably for 10 hours, or more preferably 24 hours.

The solubility of the solid oxidized glutathione salt of the present invention in water at temperature of 25° C. can be calculated according to the following formula, and the solubility is, for example, 10 mass % or more, preferably 20 mass % or more, and more preferably 30 mass % or more. The upper limit of the solubility is not particularly limited, but the upper limit may be, for example, 80 mass % or less, and particularly 60 mass % or less.

Solubility (%)=mass of dissolved oxidized glutathione/ (mass of water+mass of dissolved oxidized glutathione)×100

In addition, the solid oxidized glutathione salt of the present invention is also characterized in that the solid state thereof can be kept even after receiving mechanical impact.

The solid oxidized glutathione salt of the present invention may be crystalline or amorphous. The solid oxidized glutathione salt may have various forms such as a powder and a granule. In addition, if necessary, the solid oxidized glutathione salt may be pulverized or crushed, or processed to be nano-particles, or encapsulated. Regardless of the content, the solid oxidized glutathione salt may contain water or a solvent, and may be hydrated or solvated. However, the salt may be preferably a nonhydrate or a nonsolvate, and may particularly preferably not have water or a solvent.

The solid oxidized glutathione salt of the present invention can be used preferably as a water-soluble powder formulation, since the salt has low deliquescency and high water solubility. The size of the powder formulation is preferably 1 cm or smaller, more preferably 1 mm or smaller, and particularly preferably 0.1 mm or smaller. The powder formulation may be dissolved all in water, or may be provided with controlled release property so as to be dissolved partially. The powder formulation of the oxidized glutathione salt contains 0.01 mass % or more, preferably 0.1 mass % or more, more preferably 1 mass % or more, and particularly preferably 3 mass % or more of oxidized glutathione. The oxidized glutathione powder formulation may contain an excipient, a lubricant, a binder and a disintegrator as other components.

An excipient is exemplified by an inorganic substance such as clay; an organic substance such as a sugar, a sugar alcohol and a polysaccharide. A sugar is exemplified by lactose, sucrose, maltose and trehalose. A sugar alcohol is exemplified by mannitol, reduced malt starch syrup, reduced palatinose, maltitol, maltol, lactitol, xylitol, sorbitol and erythritol. A polysaccharide is exemplified by β-cyclodextrin and crystalline cellulose. One or combination of two or more kinds of the above-described excipients may be arbitrarily selected.

A lubricant is exemplified by a sucrose fatty acid ester, a glycerin fatty acid ester, magnesium stearate, calcium stearate, sodium stearyl fumarate, talc, sodium lauryl sulfate and light anhydrous silicon. One or combination of two or more kinds of the lubricants may be arbitrarily selected.

A binder is exemplified by methyl cellulose, ethyl cellulose, carboxymethyl cellulose, polyvinylpyrrolidone, pullulan, an acrylic acid-based polymer, polyvinyl alcohol, gelatin, agar, gum arabic, gum arabic powder, xanthan gum, tragacanth gum, guar gum, gellan gum, locust bean gum, partially pregelatinized starch and macrogol. One or combination of two or more kinds of the binders may be arbitrarily selected.

A disintegrator is exemplified by corn starch, potato starch, carboxymethyl cellulose, carboxymethyl cellulose calcium, carboxymethyl cellulose sodium, crospovidone, croscarmellose sodium and sodium carboxymethyl starch. One or combination of two or more kinds of the disintegrators may be arbitrarily selected.

The solid oxidized glutathione salt of the present invention may be dissolved or dispersed, particularly dissolved, in water or a water-containing organic medium to be preferably used as a liquid formulation, particularly a solution formulation. The organic medium to be used in the liquid formulation is not particularly limited, and the organic medium which has having higher capability of dissolving the solid oxidized glutathione salt is preferred. The organic medium is preferably exemplified by an alcohol medium such as methanol, ethanol, n-propanol, butanol, isopropanol, ethylene glycol and glycerin; a ketone medium such as acetone, methyl ethyl ketone and diethyl ketone; an aldehyde medium such as formaldehyde, acetaldehyde and formalin; an ester medium such as ethyl acetate; a hydrocarbon medium such as cyclohexane and toluene; a sulfoxide medium such as dimethyl sulfoxide; and an ether medium such as tetrahydrofuran; and particularly preferred examples thereof include an alcohol medium, a ketone medium, an aldehyde medium, an ester medium and a hydrocarbon medium. The organic medium may be used alone, or two or more thereof may be mixed for use at an arbitrary ratio.

The concentration of the oxidized glutathione in the liquid formulation is set properly depending on the use thereof, and the concentration is, for example, 0.001 mass % or higher, preferably 0.01 mass % or higher, and particularly preferably 0.1 mass % or higher. In consideration of transportation and distribution, the concentration is especially preferably 10 mass % or higher. The upper limit thereof is saturated solubility and the concentration may be selected depending on the use thereof.

The present application claims the benefit of the priority date of Japanese patent application No. 2011-146574 filed on Jun. 30, 2011, and all of the contents of the Japanese patent application No. 2011-146574 filed on Jun. 30, 2011 are incorporated by reference.

EXAMPLES

Hereinafter, the present invention is described with Examples. However, the present invention is not limited by the following Examples.

In Examples, quantitative measurement of oxidized glutathione and quantitative measurement of cation species were carried out using HPLC, and the conditions thereof were set as the following HPLC conditions 1 and 2. In addition, the following apparatuses were used for crystal analysis, melting point measurement and elementary analysis of the solid oxidized glutathione salts obtained in Examples.

1) HPLC
HPLC condition-1: Quantitative measurement of oxidized glutathione
  Column: "YMC-Pack ODS A" (length: 150 mm×inner diameter: 4.6 mm), manufactured by YMC CO., LTD.
  Column temperature: 40° C.
  Detector: UV detector (wavelength: 210 nm)
HPLC condition-2: Quantitative measurement of cation
  Column: "SHIMADZU Shim-pack (registered trade name) IC-C3" (length: 100 mm×inner diameter: 4.6 mm), manufactured by SHIMADZU CORPORATION
  Column temperature: 40° C.
  Detector: Electric conductivity detector
2) Crystal Analysis
Powder x-ray diffractometer ("Mini Flex II", manufactured by Rigaku Corporation)
3) Melting Point Measurement
Melting point measurement apparatus (Opti Melt MPA100, manufactured by Stanford Research Systems (SRS)
Measurement condition: Heating speed: 1.0° C./min
4) Elementary Analysis
Elemental analyzer ("vario MICRO cube", manufactured by Elementar Analytical)
Combustion tube temperature: 1150° C.
Reduction tube temperature: 850° C.

Example 1

Oxidized glutathione (5 g, 8.2 mmol) was dissolved in water (25 g) to prepare an aqueous solution of oxidized glutathione (30 g), and further 25% ammonia aqueous solution (0.56 g, 8.2 mmol, mole ratio relative to glutathione=1) was added thereto. While the temperature of the aqueous solution (pH=3.5) was kept at room temperature (25° C.), ethanol (90 ml, volume ratio relative to the aqueous solution=3) was added over 30 minutes; as a result, an oily product was separated from the mixed solution.

When the above ethanol-added solution was heated to 30° C., the oily product was solidified. The mixture was kept at a temperature of 30° C. as it was for 15 minutes. After the mixture was cooled to room temperature, the produced solid was collected by filtration and dried under reduced pressure to obtain 3.5 g (content: 95 mass %) of an oxidized glutathione monoammonium salt.

Melting point range: 170 to 176° C. (decomposed with being melted)

Amorphous solid (confirmed by powder x-ray diffraction)

Example 2

Oxidized glutathione (3 g, 4.9 mmol) was dissolved in water (7 g) to prepare an aqueous solution of oxidized glutathione (10 g), and further 25% ammonia aqueous solution (0.33 g, 4.9 mmol, mole ratio relative to glutathione=1) was added thereto. While the aqueous solution (pH=3.5) was heated to 40° C., methanol (20 ml, volume ratio relative to the aqueous solution=2) was added over 1 hour; as a result, a solid product was precipitated. After the mixture was kept at a temperature of 40° C. as it was for 30 minutes, the mixture was cooled to room temperature and the solid product was collected by filtration. The filtered solid product was dried under reduced pressure to obtain 2.9 g (content: 99 mass %) of an oxidized glutathione monoammonium salt.

Melting point range: 179 to 183° C. (decomposed with being melted)

Crystalline Solid

Powder x-ray diffraction [diffraction angle (2θ°), values in the parenthesis "( )" represent relative intensity]:

6.02(25), 17.4(46), 17.4(53), 17.6(72), 17.9(62), 18.7(22), 18.8(23), 18.9(21), 20.0(40), 20.2(60), 20.2(62), 21.1(42), 21.4(100), 21.9(76), 22.8(29), 22.8(29), 23(44), 23.4(96), 23.6(76), 24.7(50), 26.2(34), 28.0(27), 28.2(23), 30.8(28), 30.9(24), 35.6(34), 35.7(37), 35.8(34), 35.9(26)

Elementary Analysis

Molecular formula: $C_{20}H_{34}N_7O_{12}S_2$

Molecular weight: 630.7

Theoretical value: [N]16%, [C]38%, [S]10%

Analysis results: [N]15%, [C]38%, [S]10%

Example 3

Oxidized glutathione (3 g, 4.9 mmol) was dissolved in water (7 g) to prepare an aqueous solution of oxidized glutathione (10 g), and further 25% ammonia aqueous solution (0.33 g, 4.9 mmol, mole ratio relative to glutathione=1) was added thereto. The aqueous solution (pH=3.5) was heated to 40° C., and isopropanol (30 ml, volume ratio relative to the aqueous solution=3) was added over 1 hour; as a result, a solid product was precipitated. After the mixture was kept at a temperature of 40° C. as it was for 30 minutes, the mixture was cooled to room temperature and the solid product was collected by filtration. The filtered solid product was dried under reduced pressure to obtain 2.9 g (content: 96 mass %) of an oxidized glutathione monoammonium salt.

The results of the melting point, x-ray diffraction and elementary analysis were the same as those of the oxidized glutathione monoammonium salt described in Example 2.

Example 4

Oxidized glutathione (3 g, 4.9 mmol) was dissolved in water (7 g) to prepare an aqueous solution of oxidized glutathione (10 g), and further 25% ammonia aqueous solution (0.66 g, 9.6 mmol, mole ratio relative to glutathione=2) was added. The aqueous solution (pH=4.8) was heated to 40° C., and methanol (20 ml, volume ratio relative to the aqueous solution=2) was added over 1 hour; as a result, a solid product was precipitated. After the mixture was kept at a temperature of 40° C. as it was for 30 minutes, the mixture was cooled to room temperature and the solid product was collected by filtration. The filtered solid product was dried under reduced pressure to obtain 2.9 g (content: 95 mass %) of an oxidized glutathione monoammonium salt.

The results of the melting point, x-ray diffraction and elementary analysis were the same as those of the oxidized glutathione monoammonium salt described in Example 2.

Example 5

Oxidized glutathione (3 g, 4.9 mmol) was dissolved in water (7 g) to prepare an aqueous solution of oxidized glutathione (10 g), and further calcium hydroxide (0.36 g, 4.9 mmol, mole ratio relative to glutathione=1) was added thereto. The aqueous solution (pH=5.3) was added to methanol (100 ml, volume ratio relative to the aqueous solution=about 10) which was heated to 40° C. over 1 hour; as a result, a solid product was precipitated. After the mixture was kept at a temperature of 40° C. as it was for 30 minutes, the mixture was cooled to room temperature and the solid product was collected by filtration. The filtered solid product was dried under reduced pressure to obtain 2.9 g (content: 98 mass %) of an oxidized glutathione monocalcium salt.

Melting point range: 194 to 205° C. (decomposed with being melted)

Amorphous solid (confirmed by powder x-ray diffraction)

Example 6

Oxidized glutathione (3 g, 4.9 mmol) was dissolved in water (7 g) to prepare an aqueous solution of oxidized glutathione (10 g), and further calcium hydroxide (0.18 g, 2.5 mmol, mole ratio relative to glutathione=0.5) was added thereto. The aqueous solution (pH=3.4) was added to methanol (100 ml, volume ratio relative to the aqueous solution=about 10) which was heated to 40° C. over 1 hour; as a result, a solid product was precipitated. After the mixture was kept at a temperature of 40° C. as it was for 30 minutes, the mixture was cooled to room temperature and the solid product was collected by filtration. The filtered solid product was dried under reduced pressure to obtain 2.9 g (content: 97 mass %) of an oxidized glutathione hemicalcium salt.

Melting point range: 188 to 195° C. (decomposed with being melted)

Amorphous solid (confirmed by powder x-ray diffraction)

Elementary Analysis

Molecular formula: $C_{20}H_{30}N_6O_{12}S_2Ca_{0.5}$

Molecular weight: 631.7

Theoretical value: [N]13%, [C]38%, [S]10%

Analysis results: [N]13%, [C]39%, [S]10%

Example 7

Oxidized glutathione (5 g, 8.2 mmol) was dissolved in water (25 g) to prepare an aqueous solution of oxidized glutathione (30 g), and further magnesium hydroxide (0.4 g, 8.2 mmol, mole ratio relative to glutathione=1) was added thereto. The aqueous solution (pH=4.7) was added to methanol (100 ml, volume ratio relative to the aqueous solution=3.5) having a temperature of 25° C. over 30 minutes; as a result, a gelatinous precipitate was obtained. After the supernatant was removed by decantation, the residue was dried under reduced pressure with heating at 50° C. for 6 hours, to obtain 5.0 g (content: 95 mass %) of an oxidized glutathione monomagnesium salt.

Melting point range: 186 to 197° C. (decomposed with being melted)

Amorphous Solid (Confirmed by Powder X-Ray Diffraction)

Example 8

Oxidized glutathione (5 g, 8.2 mmol) was dissolved in water (25 g) to prepare an aqueous solution of oxidized glutathione (30 g), and further magnesium hydroxide (0.24 g, 4.1 mmol, mole ratio relative to glutathione=0.5) was added thereto. The aqueous solution (pH=3.4) was added to methanol (100 ml, volume ratio relative to the aqueous solution=3.5) which was heated to 40° C. over 1 hour; as a result, a solid product was precipitated. After the mixture was kept at a temperature of 30° C. as it was for 30 minutes, the mixture was cooled to room temperature and the solid product was collected by filtration. The filtered solid product was dried under reduced pressure to obtain 4.8 g (content: 98 mass %) of an oxidized glutathione hemimagnesium salt.

Melting point range: 179 to 186° C. (decomposed with being melted)

Amorphous solid (confirmed by powder x-ray diffraction)

Example 9

Reduced glutathione (20 g, 65 mmol) was dissolved in water (180 g) to prepare an aqueous solution of reduced glutathione (200 g), and further 25% ammonia aqueous solution (4.4 g, 65 mmol, mole ratio relative to glutathione=1) was added thereto so that the pH of the solution was adjusted to 7.8. Then, the solution was stirred under air atmosphere to oxidize the reduced glutathione. After 35% hydrochloric acid (3.4 g, 33 mmol) was added to the aqueous solution so that the pH became 3.5, the temperature was increased to 40° C. Methanol (400 ml, volume ratio relative to the aqueous solution=2) was added over 1 hour thereto; as a result, a solid product was precipitated. After the mixture was kept at a temperature of 40° C. as it was for 30 minutes, the mixture was cooled to room temperature and the solid product was collected by filtration. The filtered solid product was dried under reduced pressure to obtain 19.6 g (content: 96 mass %) of an oxidized glutathione monoammonium salt.

The results of the melting point, x-ray diffraction and elementary analysis were the same as those of the oxidized glutathione monoammonium salt described in Example 2.

Example 10

Oxidized glutathione (3.5 kg, 5.7 mol) was dissolved in water (14 kg) to prepare an aqueous solution of oxidized glutathione, and further 25% ammonia aqueous solution (0.39 kg, 5.7 mol, mole ratio relative to glutathione=1) was added thereto. While the aqueous solution (pH=3.5) was heated to 60° C. and stirred with agitation power of 1 kw/m$^3$, methanol (17.5 kg, 21 L, volume ratio relative to the aqueous solution=1.3) was added over 1 hour; as a result, a solid product was precipitated. After the mixture was kept at a temperature of 60° C. with stirring for 2 hours, the mixture was cooled to room temperature and the solid product was collected by filtration. The filtered solid product was dried under reduced pressure to obtain 3.6 kg (content: 99 mass %) of an oxidized glutathione monoammonium salt.

The results of the melting point, x-ray diffraction and elementary analysis were the same as those of the oxidized glutathione monoammonium salt described in Example 2.

Example 11

Oxidized glutathione (3.5 kg, 5.7 mol) was dissolved in water (14 kg) to prepare an aqueous solution of oxidized glutathione, and further 25% ammonia aqueous solution (0.39 kg, 5.7 mol, mole ratio relative to glutathione=1) was added thereto. While the aqueous solution (pH=3.5) was heated to 50° C. and stirred with agitation power of 1 kw/m$^3$, methanol (17.5 kg, 21 L, volume ratio relative to the aqueous solution=1.3) was added over 1 hour; as a result, a solid product was precipitated. After the mixture was kept at a temperature of 50° C. with stirring for 2 hours, the mixture was cooled to room temperature and the solid product was collected by filtration. The filtered solid product was dried under reduced pressure to obtain 3.6 kg (content: 99 mass %) of an oxidized glutathione monoammonium salt.

The results of the melting point, x-ray diffraction and elementary analysis were the same as those of the oxidized glutathione monoammonium salt described in Example 2.

Example 12

Oxidized glutathione (3.5 kg, 5.7 mol) was dissolved in water (14 kg) to prepare an aqueous solution of oxidized glutathione, and further 25% ammonia aqueous solution (0.39 kg, 5.7 mol, mole ratio relative to glutathione=1) was added thereto. While the aqueous solution (pH=3.5) was heated to 45° C. and stirred with agitation power of 1 kw/m$^3$, methanol (17.5 kg, 21 L, volume ratio relative to the aqueous solution=1.3) was added over 1 hour; as a result, a mixture of a solid product and an oily product was precipitated to be in an emulsified state. After the mixture was kept at a temperature of 45° C. for 1 hour, the oily product was wholly solidified. Then, the mixture was cooled to room temperature and the solid product was collected by filtration. The melting point of the filtered solid product was measured and the solid product was analyzed by X-ray diffraction; as a result, it was confirmed that the solid product was an oxidized glutathione monoammonium salt.

Comparative Example 1

Oxidized glutathione (5 g, 8.2 mmol) was dissolved in water (25 g) to prepare an aqueous solution of oxidized glutathione (30 g), and further 25% ammonia aqueous solution (0.56 g, 8.2 mmol, mole ratio relative to glutathione=1) was added thereto. The obtained aqueous solution was subjected to freeze-dry to obtain an oxidized glutathione monoammonium salt; however, the obtained oxidized glutathione monoammonium salt soon became oily and could not be handled as a solid.

Comparative Example 2

Oxidized glutathione (3 g, 4.9 mmol) was dissolved in water (7 g) to prepare aqueous solution of oxidized glutathione (10 g), and further 25% ammonia aqueous solution (0.33 g, 4.9 mmol, mole ratio relative to glutathione=1) was added thereto. While the temperature of the obtained aqueous solution was maintained at room temperature, i.e. 25° C., methanol (20 ml, volume ratio relative to the aqueous solution=2) was added thereto; as a result, an oily substance was settled out and a solid substance could not be obtained.

Comparative Example 3

Oxidized glutathione (3 g, 4.9 mmol) was dissolved in water (7 g) to prepare an aqueous solution of oxidized glutathione (10 g), and further sodium hydroxide (0.39 g, 9.8 mmol, mole ratio relative to glutathione=1) was added thereto. The aqueous solution was heated to 40° C., and methanol (60 ml, volume ratio relative to the aqueous solution=6) was added thereto over 1 hour. However, an oily substance was settled out and a solid substance could not be obtained.

Evaluation 1: Solubility in water at 25° C. under normal pressure and deliquescency of oxidized glutathione salt (1) Solubility Each of the powders of the solid-state oxidized glutathione salt obtained in the above respective Examples was dissolved in water until the powder was not further dissolved. After each slurry was stirred for 30 minutes or longer, the supernatant was obtained and the concentrations of each oxidized glutathione and salt were calculated using HPLC. For comparison, the solubilities of the following conventionally known solid oxidized glutathiones were investigated in the same manner as the above.

Oxidized glutathione anhydride, prepared according to the method of Reference Example 1 disclosed in WO 2003/035674 (Patent Document 3)

Oxidized glutathione monohydrate, prepared according to the method of Example 1 disclosed in WO 2003/035674 (Patent Document 3)

Oxidized glutathione disodium salt, manufactured by Sigma-Aldrich Co., LLC.

(2) Deliquescency

Each of the powders of the solid-state oxidized glutathione salt obtained in the above respective Examples was allowed to stand in atmospheric condition of a temperature of 25° C., normal pressure and a relative humidity of 75% RH. After 2 hours or 24 hours, it was determined whether or not deliquescence was is present by observing the occurrence of shape change with naked eyes. For comparison, the deliquescencies of the above commercially available solid oxidized glutathiones were investigated in the same manner.

The results are demonstrated in Table 1.

TABLE 1

| | | Solubility | Deliquescency | |
|---|---|---|---|---|
| | | (mass %, at 25° C., in water) | 2 hours | 24 hours |
| Example 1 | Oxidized glutathione monoammonium salt (amorphous) | — | no | no |
| Example 2 | Oxidized glutathione monoammonium salt (crystal) | 34.8 | no | no |
| Example 5 | Oxidized glutathione monocalcium salt | 58.6 | no | no |
| Example 6 | Oxidized glutathione hemicalcium salt | 58 | no | no |
| Example 7 | Oxidized glutathione monomagnesium salt | 41 | no | slightly deliquescent |
| Example 8 | Oxidized glutathione hemimagnesium salt | 42.8 | no | slightly deliquescent |
| Control | Oxidized glutathion anhydride | 49.7 | deliquescent | deliquescent |
| | Oxidized glutathion monohydrate | 2.4 | no | no |
| | Oxidized glutathion disodium salt | 51.1 | deliquescent | deliquescent |

It is clear from Table 1 that conventional solid oxidized glutathiones (controls) have either high deliquescency or low water solubility, and fail to satisfy both of high water solubility and low deliquescency. The solid oxidized glutathione salts of Examples can satisfy both of high water solubility and low deliquescency.

INDUSTRIAL APPLICABILITY

The oxidized glutathione salt of the present invention is useful as a health food product, a pharmaceutical product, a cosmetic product, a fertilizer product and the like, or an intermediate for producing the products.

The invention claimed is:

1. A method for producing a solid oxidized glutathione salt, comprising:
heating an oxidized glutathione at 30° C. or higher while the oxidized glutathione is contacted with an aqueous medium in the presence of a substance for providing a cation, to produce a salt of the oxidized glutathione and the cation as a solid,
wherein the aqueous medium comprises at least one of water and a water-soluble medium, and
the cation is at least one selected from the group consisting of an ammonium cation, a calcium cation and a magnesium cation.

2. The method according to claim 1, wherein the oxidized glutathione is heated at 30° C. or higher for 0.25 hours or longer.

3. The method according to claim 1, wherein the aqueous medium comprises at least one water-soluble medium selected from the group consisting of an alcohol medium and a ketone medium.

4. The method according to claim 3, wherein the aqueous medium comprises at least one alcohol medium selected from the group consisting of methanol, ethanol, propanol and butanol.

5. A solid oxidized glutathione salt, comprising consisting of:
oxidized glutathione; and
at least one cation selected from the group consisting of an ammonium cation, a calcium cation and a magnesium cation,
wherein the solid oxidized glutathione salt is in a solid state at room temperature.

6. The solid oxidized glutathione salt according to claim 5, wherein the solid oxidized glutathione salt does not deliquesce when the solid oxidized glutathione salt is maintained at 25° C., at ordinary pressure and at a relative humidity of 75% RH for 2 hours or longer.

7. The solid oxidized glutathione salt according to claim 5, wherein the solid oxidized glutathione salt is a monoammonium salt of oxidized glutathione.

8. The solid oxidized glutathione salt according to claim 5, wherein the solid oxidized glutathione salt is a hemicalcium salt or a monocalcium salt of oxidized glutathione.

9. The solid oxidized glutathione salt according to claim 5, wherein the solid oxidized glutathione salt is a hemimagnesium salt or a monomagnesium salt of oxidized glutathione.

10. A powder formulation, comprising:
the solid oxidized glutathione salt according to claim 5, wherein a content of oxidized glutathione is 0.01 mass % or more.

11. A method of producing a liquid formulation, comprising:
dissolving or dispersing the solid oxidized glutathione salt according to claim 5 in water or in an organic medium comprising water.

12. The method according to claim 11, wherein the solid oxidized glutathione salt is dissolved or dispersed in the organic medium which is at least one selected from the group consisting of an alcohol medium, a ketone medium, an aldehyde medium, an ester medium, a hydrocarbon medium, a sulfoxide medium and an ether medium.

13. The method according to claim 2, wherein the aqueous medium comprises at least one water-soluble medium selected from the group consisting of an alcohol medium and a ketone medium.

14. The method according to claim 3, wherein the aqueous medium comprises at least one ketone medium selected from the group consisting of acetone and methyl ethyl ketone.

15. The solid oxidized glutathione salt according to claim 6, wherein the solid oxidized glutathione salt is a monoammonium salt of oxidized glutathione.

16. The solid oxidized glutathione salt according to claim 6, wherein the solid oxidized glutathione salt is a hemicalcium salt or a monocalcium salt of oxidized glutathione.

17. The solid oxidized glutathione salt according to claim 6, wherein the solid oxidized glutathione salt is a hemimagnesium salt or a monomagnesium salt of oxidized glutathione.

18. A solid oxidized glutathione salt produced by the method according to claim 1.

19. A powder formulation, comprising:
the solid oxidized glutathione salt according to claim 18, wherein a content of oxidized glutathione is 0.01 mass % or more.

20. A method of producing a liquid formulation, comprising:
dissolving or dispersing the solid oxidized glutathione salt according to claim 18 in water or in an organic medium comprising water.

* * * * *

UNITED STATES PATENT AND TRADEMARK OFFICE
CERTIFICATE OF CORRECTION

| | |
|---|---|
| PATENT NO. | : 9,303,062 B2 |
| APPLICATION NO. | : 14/129474 |
| DATED | : April 5, 2016 |
| INVENTOR(S) | : Taku Mouri et al. |

It is certified that error appears in the above-identified patent and that said Letters Patent is hereby corrected as shown below:

Claims

Column 18, lines 12-13, claim 5, "A solid oxidized glutathione salt, comprising consisting of:" should read --A solid oxidized glutathione salt, consisting of:--

Signed and Sealed this
Nineteenth Day of July, 2016

Michelle K. Lee
*Director of the United States Patent and Trademark Office*